(12) United States Patent
Kim et al.

(10) Patent No.: US 8,655,425 B2
(45) Date of Patent: Feb. 18, 2014

(54) OPTICAL SENSOR BIOSIGNAL MEASUREMENT APPARATUS AND METHOD OF CONTROLLING OPTICAL SENSOR OF THE APPARATUS

(75) Inventors: Youn Ho Kim, Hwaseong-si (KR); Kun Soo Shin, Seongnam-si (KR); Kun Kook Park, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1408 days.

(21) Appl. No.: 12/010,560

(22) Filed: Jan. 25, 2008

(65) Prior Publication Data
US 2008/0275322 A1   Nov. 6, 2008

(30) Foreign Application Priority Data
May 3, 2007 (KR) .................. 10-2007-0042976

(51) Int. Cl.
*A61B 5/00* (2006.01)
(52) U.S. Cl.
USPC ............................ 600/310; 600/324; 356/73
(58) Field of Classification Search
USPC ...................... 600/310, 324; 356/73
See application file for complete search history.

(56) References Cited

U.S. PATENT DOCUMENTS

| | | | | |
|---|---|---|---|---|
| 5,045,683 | A * | 9/1991 | Kanda | 250/205 |
| 6,014,204 | A * | 1/2000 | Prahl et al. | 356/73 |
| 6,188,434 | B1 | 2/2001 | Tsuchiya | |
| 2001/0041843 | A1 * | 11/2001 | Modell et al. | 600/473 |
| 2002/0071185 | A1 * | 6/2002 | Chretien et al. | 359/629 |
| 2006/0206018 | A1 * | 9/2006 | Abul-Haj et al. | 600/316 |
| 2006/0258922 | A1 * | 11/2006 | Mason et al. | 600/323 |
| 2007/0225560 | A1 * | 9/2007 | Avni et al. | 600/118 |

FOREIGN PATENT DOCUMENTS

| | | |
|---|---|---|
| JP | 02-295542 | 12/1990 |
| JP | 07-136152 | 5/1995 |
| JP | 07-063450 | 7/1995 |
| JP | 2001-061796 | 3/2001 |
| KR | 10-1997-0072987 | 11/1997 |
| KR | 10-2000-0039895 | 7/2000 |
| KR | 10-2000-0054856 | 9/2000 |
| KR | 10-2003-0054607 | 7/2003 |
| KR | 10-2007-0045723 | 5/2007 |

OTHER PUBLICATIONS

Korean Notice of Allowance issued on Jul. 10, 2008 in corresponding Korean Patent Application 10-2007-0042976.

* cited by examiner

*Primary Examiner* — Max Hindenburg
*Assistant Examiner* — Renee Danega
(74) *Attorney, Agent, or Firm* — Staas & Halsey LLP (57) ABSTRACT

An optical sensor biosignal measurement apparatus including an optical sensor having a luminous element to emit light towards the skin of a user and a photo detector to detect light from the skin of the user; a light quantity adjustment member to adjust an optical transmission area of the photo detector; and a light quantity controller to detect the quantity of light detected by the photo detector, and control the light quantity adjustment member to adjust the optical transmission area of the photo detector according to the quantity of light is provided.

21 Claims, 5 Drawing Sheets

OPTICAL SENSOR BIOSIGNAL MEASUREMENT APPARATUS AND METHOD OF CONTROLLING OPTICAL SENSOR OF THE APPARATUS

CROSS-REFERENCE TO RELATED APPLICATIONS

This application claims the benefit of Korean Patent Application No. 10-2007-0042976, filed on May 3, 2007, in the Korean Intellectual Property Office, the disclosure of which is incorporated herein by reference.

BACKGROUND

1. Field

The embodiments relate to an optical sensor biosignal measurement apparatus and a method of controlling an optical sensor of the apparatus, and more particularly, to an optical sensor biosignal measurement apparatus which can appropriately adjust an optical transmission area of a photo detector of an optical sensor according to the strength of light detected by the photo detector, and thereby can reduce noise caused by external environments, such as interfering light, etc., and a method of controlling an optical sensor of the apparatus.

2. Description of the Related Art

As used in the present specification, the term "Ubiquitous" is an information communication environment where a user can be free to access networks at any place without being conscious of the surrounding networks or computers. If Ubiquitous is commercialized, anyone can readily use information technology not only at home or in a car, but also even on a mountaintop. Also, the commercialization of Ubiquitous may expand the information technology industry or the scope corresponding thereto by increasing the number of computer users who are connected to networks. Because of the advantage that users can access networks without restriction to time and place, not to mention its portability and convenience, countries worldwide are expanding development and competing in Ubiquitous-related technology now.

Ubiquitous-related technology may be applied to myriad fields in human life. In particular, Ubiquitous-HealthCare (hereinafter, U-HealthCare) has recently been in the spotlight as a notable technology area due to the "well-being" boom. U-HealthCare is Ubiquitous technology which enables anyone to readily receive medical services at any time and at any place by installing medical service-related chips or sensors in places within the user's living space. With U-HealthCare, various types of medical attention, such as physical examinations, disease management, emergency care, consultation with a doctor, etc., which currently are only performed in hospitals, may be naturally integrated into our daily lives, and thus may be accomplished without going to a hospital.

For example, a diabetic may wear a belt having a blood-sugar management system for blood-sugar management. A blood-sugar sensor attached to the belt may check the blood-sugar of the diabetic upon a specified occasion, and may calculate the amount of required insulin corresponding thereto. When the blood-sugar of the diabetic becomes drastically low or high, the belt may provide the blood-sugar information to his/her attending physician using a wireless network, and the attending physician who has received the blood-sugar information may write out an optimal prescription or take an optimal action for the medical emergency.

As an example of U-HealthCare, a portable biosignal measurement device to measure the user's biosignal using an optical sensor is being widely utilized. The user may carry the portable biosignal measurement device at all times and measure various types of biosignals, and thereby may prepare for an emergency situation. Accordingly, the portable biosignal measurement device may be regarded as a device capable of showing advantages of U-HealthCare.

The portable biosignal measurement apparatus includes a photoplethysmography (PPG) measurement device. A PPG includes information about a level of peripheral vasoconstriction, and increase and decrease in a cardiac output. Therefore, a physiological status associated with an arterial tube may be understood using the PPG measurement device. Also, the PPG measurement device may be generally utilized as an auxiliary diagnostic device for a particular disease.

Generally, a PPG signal may be measured from a user's finger, earlobe, etc. Specifically, a detector may detect the user's PPG signal by detecting light, passing through the finger, earlobe, etc., from a light source. However, when a PPG signal is weak, for example, a PPG signal detected from the earlobe, etc., a normal PPG signal may not be detected due to interference noise of disturbance light or motion.

When a measurement device measures a PPG signal from a body portion corresponding to a weak signal source, such as the earlobe, etc., a level of the PPG signal may be less than noise of the measurement device or the interference noise of the disturbance light or the motion. Therefore, although the weak PPG signal is amplified, the system noise is also amplified and thus a desired PPG signal may not be accurately detected.

As described above, the quantity of incidence light is one of the most important elements to determine a signal-to-noise ratio (SNR) when measuring a PPG signal using light. A conventional PPG measurement apparatus uses a method of initially adjusting the quantity of light in an initial state of measurement, that is, automatically selecting the quantity of light so that a PPG signal may be generated within an observance range, and thereby fixing the quantity of light.

However, when the disturbance light exists, it may be difficult to acquire a PPG signal within the observance range due to the disturbance light even though the quantity of light from a luminous element is adjusted. Particularly, when measuring a PPG signal while doing an outdoor activity, it may be more difficult to accurately measure a PPG signal due to various types of disturbance light effect, such as an external illumination, sunlight, a shadow, etc.

Accordingly, there is a need for an optical sensor biosignal measurement apparatus which can reduce the effect of disturbance light and thereby more accurately measure a biosignal when measuring the biosignal using an optical sensor.

SUMMARY

An aspect of the present invention provides an optical sensor biosignal measurement apparatus which can install a diaphragm in a photo detector of an optical sensor, appropriately adjust an optical transmission area of the photo detector via the diaphragm, and reduce effects of disturbance light, and thereby can more accurately measure a biosignal without restriction on time and occasion, and a method of controlling an optical sensor of the apparatus.

Another aspect of the present invention also provides an optical sensor biosignal measurement apparatus which can install at least one polymer-dispersed liquid crystal (PDLC) unit in a photo detector of an optical sensor, appropriately adjust an optical transmission area of the photo detector via the at least one PDLC unit, and reduce effects of disturbance light, and thereby can more accurately measure a biosignal without restriction on time and occasion, and a method of controlling an optical sensor of the apparatus.

Another aspect of the present invention also provides an optical sensor biosignal measurement apparatus which can install a liquid crystal display (LCD) unit in a photo detector of an optical sensor, appropriately adjust an optical transmission area of the photo detector via the LCD unit, and reduce effects of disturbance light, and thereby can more accurately measure a biosignal without restriction on time and occasion, and a method of controlling an optical sensor of the apparatus.

Additional aspects and/or advantages will be set forth in part in the description which follows and, in part, will be apparent from the description, or may be learned by practice of the invention.

The foregoing and/or other aspects are achieved by providing an optical sensor biosignal measurement apparatus including: an optical sensor having a luminous element to emit light towards the skin of a user and a photo detector to detect light from the skin of the user; a light quantity adjustment member to adjust an optical transmission area of the photo detector; and a light quantity controller to detect the quantity of light detected by the photo detector, and control the light quantity adjustment member to adjust the optical transmission area of the photo detector according to the quantity of light.

The foregoing and/or other aspects are achieved by providing a method of controlling an optical sensor of an optical sensor biosignal measurement apparatus, the method including: detecting light from skin of a user using a photo detector wherein the photo detector includes a light quantity adjustment member; detecting a DC level of the detected quantity of light; comparing the DC level of the quantity of light with a threshold value for a predetermined period of time; and controlling the light quantity adjustment member to reduce an optical transmission area of the photo detector when the DC level of the quantity of light is greater than the threshold value for at least as long as the predetermined period of time, as a, result of the comparison.

The foregoing and/or other aspects are achieved by providing a method of controlling an optical sensor of an optical sensor biosignal measurement apparatus, the method including: detecting a quantity of light from skin of a user with a photo detector; and reducing an optical transmission area of the photo detector when a DC level of the detected quantity of light exceeds a first threshold value for a predetermined period of time.

The method may further include eliminating a peak value of the DC level of the quantity of light when the DC level of the detected quantity of light exceeds the first threshold value for less than the predetermined period of and generating biosignal information based on the DC level of the quantity of light, excluding the eliminated peak value of the DC level of the quantity of light.

The method may include increasing a strength of the light emitted toward the skin of the user to detect the quantity of light form the skin of the user when the detected quantity of light is less than a second threshold value.

The foregoing and/or other aspects are achieved by providing an optical sensor biosignal measurement apparatus, including: a light quantity controller adjusting an optical transmission area of a photo detector detecting a quantity of light from skin of a user, according to the detected quantity of light detected from the skin of the user.

BRIEF DESCRIPTION OF THE DRAWINGS

These and/or other aspects, features, and advantages will become apparent and more readily appreciated from the following description of the embodiments, taken in conjunction with the accompanying drawings of which.

DETAILED DESCRIPTION OF THE EMBODIMENTS

Reference will now be made in detail to the embodiments, examples of which are illustrated in the accompanying drawings, wherein like reference numerals refer to the like elements throughout. The embodiments are described below to explain the present invention by referring to the figures.

An optical sensor biosignal measurement apparatus according to the embodiments may be included in any one of a mobile communication terminal, a personal digital assistant (PDA), a portable game device, an MPEG audio layer-3 (MP3) player, a personal multimedia player (PMP), a Digital Multimedia Broadcasting (DMB) terminal, etc. Also, the optical sensor biosignal measurement apparatus may not be installed in the devices, but may be designed to have a stand-alone configuration.

Also, the optical sensor biosignal measurement apparatus may measure various types of biosignals, such as a user's photoplethysmography (PPG) signal, or oxygen saturation by using an optical sensor. In this instance, the optical sensor includes a luminous element and a photo detector.

Hereinafter, embodiments will be described in detail with reference to the accompanying drawings.

Figure 1:
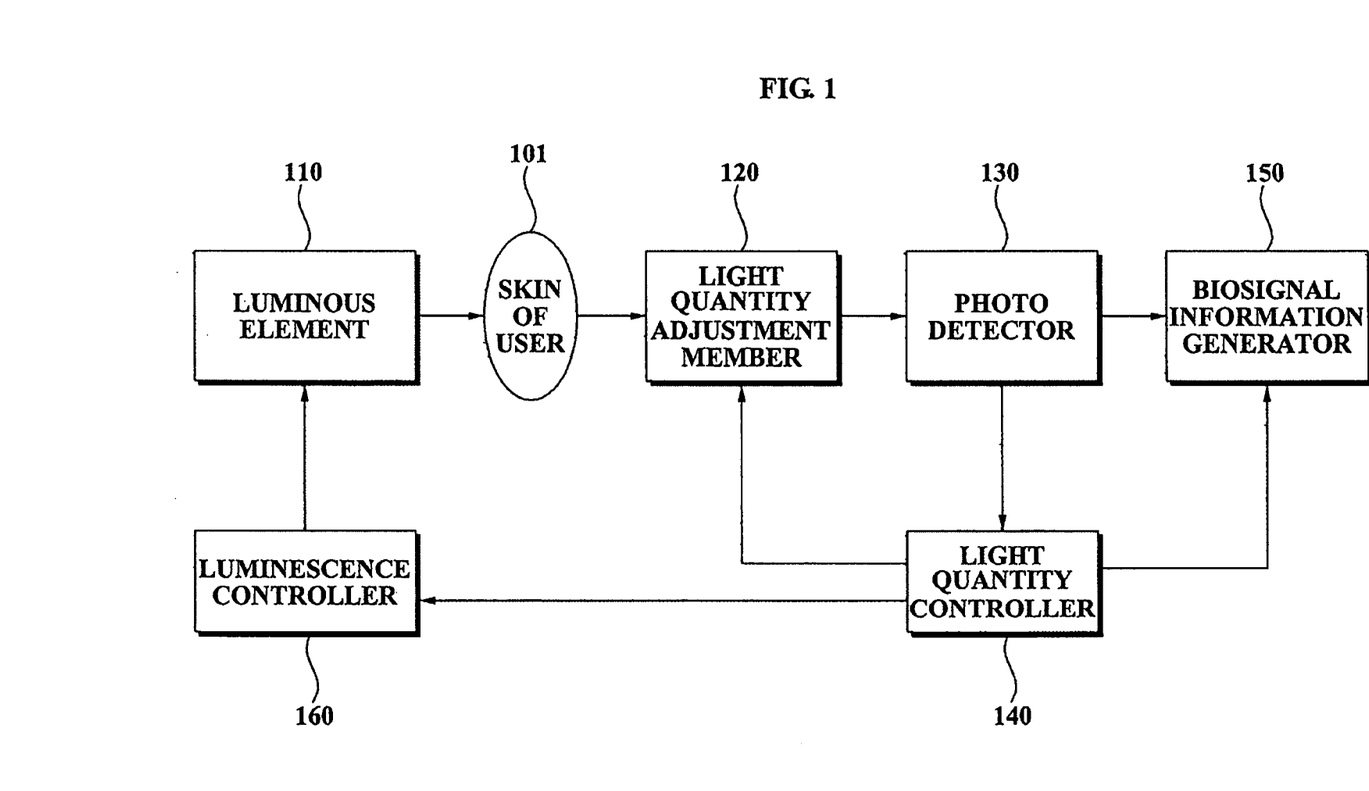
FIG. 1 is a block diagram illustrating a configuration of an optical sensor biosignal measurement apparatus according to an embodiment.

FIG. 1 is a block diagram illustrating a configuration of an optical sensor biosignal measurement apparatus according to an embodiment.

The optical sensor biosignal measurement apparatus according to the present embodiment includes a luminous element 110, a light quantity adjustment member 120, a photo detector 130, a light quantity controller 140, a biosignal information generator 150, and a luminescence controller 160. In this instance, the biosignal information generator 150 and the luminescence controller 160 are additional elements of the optical sensor biosignal measurement apparatus and not essential elements of the optical sensor biosignal measurement apparatus.

The luminous element 110 emits light towards the skin of a user 101. In this instance, the luminous element 110 may include a light emitting diode (LED, not shown). Also, in addition to the LED, the luminous element 110 may include any type of device which can emit light towards the skin of the user to measure a biosignal. However, in the present specification, the luminous element 110 including the LED will be described as an example, which is for convenience of description.

The photo detector 130 detects the light from the skin of the user 101. Specifically, the photo detector 130 detects the light which is emitted from the luminous element 110 towards the skin of the user 101 and is thereby scattered or reflected.

The light quantity adjustment member 120 adjusts an optical transmission area of the photo detector 130. Specifically, the optical quantity adjustment member 120 may adjust the optical transmission area of the photo detector 130 which detects the light from the skin of the user 101. For the above operation, the light quantity adjustment member 120 may be configured as any one of a diaphragm, at least one polymer-dispersed liquid crystal (PDLC) unit, and a liquid crystal display (LCD) unit, which will be described in detail with reference to FIGS. 2 through 4.

Figure 2:
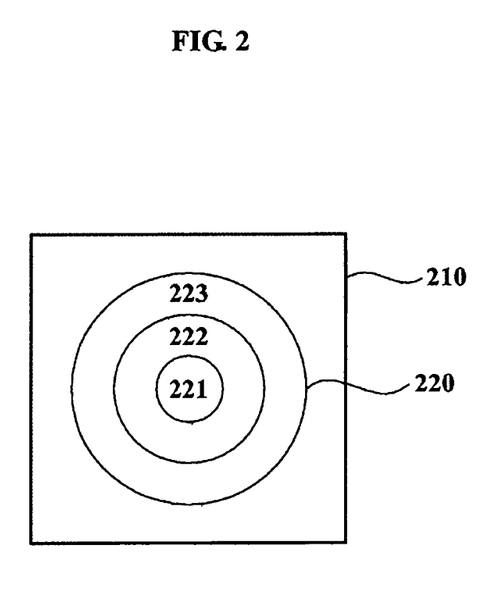
FIG. 2 illustrates a light quantity adjustment member configured as a diaphragm according to an embodiment.

FIG. 2 illustrates the light quantity adjustment member 120 configured as a diaphragm 220 according to an embodiment.

As described above, the light quantity adjustment member 120 may be configured as the diaphragm 220. In this instance, the diaphragm 220 may be attached onto one surface of a photo detector 210 which contacts the skin of a user and thereby detects light from the skin of the user.

Also, the diaphragm 220 may adjust an optical transmission area of the photo detector 210 through an opening/closing operation, which is the same as in a general diaphragm installed in a camera and the like. For example, when the diaphragm 220 is opened in a first area 221, the optical transmission area of the photo detector 210 may be the first area 221. Also, when the diaphragm 220 is opened in a second area 222, the optical transmission area of the photo detector 210 may be the second area 222. Also, when the diaphragm 220 is opened in a third area 223, the optical transmission area of the photo detector 210 may be the third area 223. In this instance, the second area 222 includes the first area 221, and the third area 223 includes both the second area 222 and the first area 221.

As described above, the light quantity adjustment member 120 according to the present embodiment may be configured as the diaphragm 220 and may adjust the optical transmission area of the photo detector 210.

Figure 3:
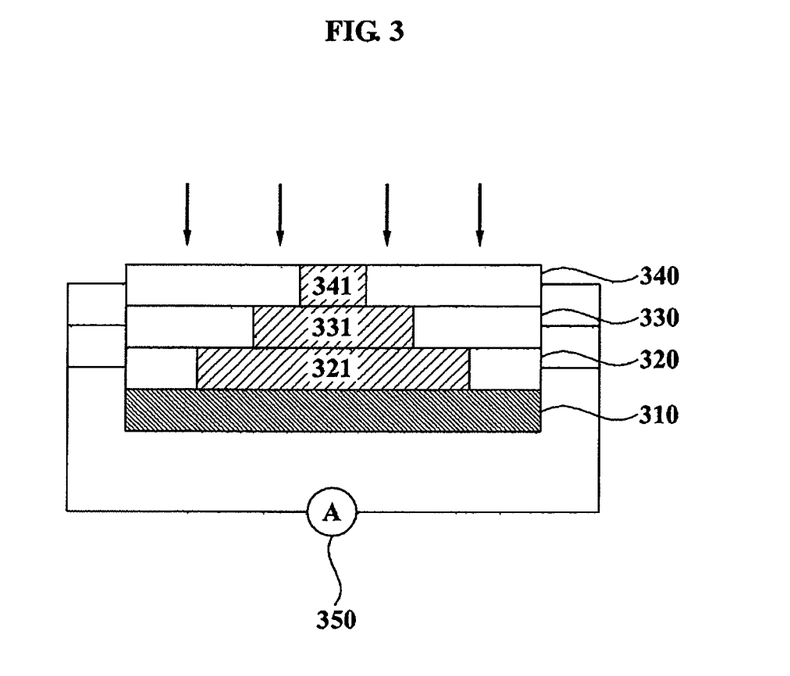
FIG. 3 illustrates a side view of a light quantity adjustment member configured as at least one PDLC unit according to another embodiment.

FIG. 3 illustrates a side view of the light quantity adjustment member 120 configured as at least one PDLC unit according to another embodiment.

As shown in FIG. 3, the light quantity adjustment member 120 may include a first PDLC unit 320, a second PDLC unit 330, and a third PDLC unit 340.

As well-known in the art, PDLC indicates polymer-dispersed liquid crystal, and is one type of a liquid cell used for LCDs. The optical transmittance of PDLC may change according to a supplied current. Specifically, when no current is supplied, liquid molecules of PDLC are irregularly arranged and thus the optical transmittance of PDLC is reduced and the light may not be transmitted. Also, when the current is supplied, the liquid molecules of PDLC are arranged in a regular direction and thus the reflective index of quantum matches and the light may be transmitted.

Accordingly, it is possible to adjust the optical transmission area of a photo detector 310 by using the features of PDLC. As shown in FIG. 3, the first PDLC unit 320 may include PDLC of a first area 321 in an optical transmission unit, such as glass, etc. Also, the second PDLC unit 330 may include PDLC of a second area 331 in the optical transmission unit, such as glass, etc. Also, the third PDLC unit 340 may include PDLC of a third area 341 in the optical transmission unit, such as glass, etc.

In this case, it is possible to adjust the optical transmission area of the photo detector 310 by controlling the current to be supplied to each of the first PDLC unit 320, the second PDLC unit 330, and the third PDLC unit 340.

For example, when a current source A 350 does not supply current to the first PDLC unit 320, the optical transmission area of the photo detector 310 may be either the second area 331 or the third area 341, excluding the first area 321. Also, when the current source 350 supplies the current to the first PDLC unit 320 without supplying the current to the second PDLC unit 330, the optical transmission area of the photo detector 310 may be either the first area 321 or the third area 341, excluding the second area 331. Also, when the current source 350 supplies the current to the first PDLC unit 320 and the second PDLC unit 330 without supplying the current to the third PDLC unit 340, the optical transmission area of the photo detector 310 may be either the first area 321 or the second area 331, excluding the third area 341.

As described above, the light quantity adjustment member 120 according to the present embodiment may adjust the optical transmission area of the photo detector 310 via at least one PDLC unit.

Figure 4:
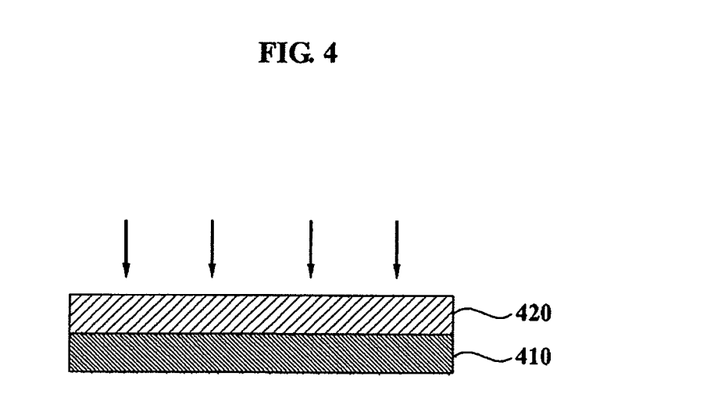
FIG. 4 illustrates a side view of a light quantity adjustment member configured as an LCD unit according to still another embodiment.

FIG. 4 illustrates a side view of the light quantity adjustment member 120 configured as an LCD unit 420 according to still another embodiment.

According to the present embodiment, the light quantity adjustment member 120 may be configured as the LCD unit 420. As well-known in the art, an LCD may be constructed to emit any one of hundreds of colors, and be constructed to have minute optical transmittance. Accordingly, it is possible to install the LCD unit 420 on one surface of a photo detector 410, which detects light from the skin of a user, and thereby makes it possible to adjust the optical transmission area or the optical transmittance of the photo detector 410.

Referring again to FIG. 1, the light quantity controller 140 may detect the quantity of light detected by the photo detector 130, and may control the light quantity adjustment member 120 to adjust the optical transmission area of the photo detector 130 according to the quantity of light.

For the above operation, the light quantity controller 140 detects a DC level of the quantity of light detected by the photo detector 130. Also, the light quantity controller 140 compares the DC level of the quantity of light with a threshold value for a predetermined period of time.

When the DC level of the quantity of light is greater than the threshold value for at least as long as the predetermined period of time as a result of the comparison, the light quantity controller 140 controls the light quantity adjustment member 120 to reduce the optical transmission area of the photo detector 130. Conversely, when the DC level of the quantity of light is in excess of the threshold value for less than the predetermined period of time as a result of the comparison, the light quantity controller 140 controls the biosignal information generator 150 to eliminate the DC level of the quantity of light in excess of the threshold value and thereby generate the user's biosignal information, which will be described in detail with reference to FIG. 5.

Figure 5:
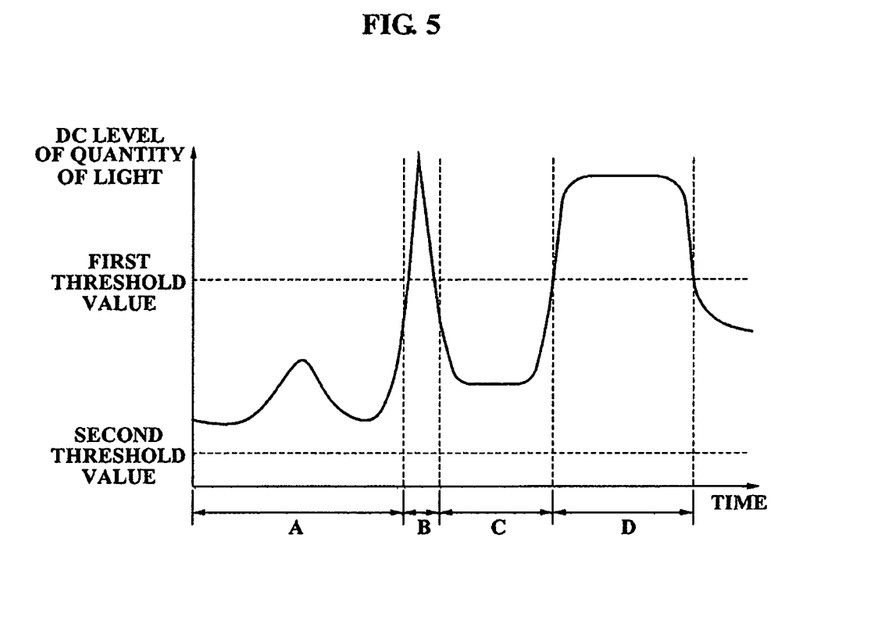
FIG. 5 is a graph illustrating a change in a DC level of the quantity of light over time, detected from the skin of a user via a photo detector when measuring a PPG signal, according to an embodiment.

FIG. 5 is a graph illustrating a change in a DC level of the quantity of light over time, detected from the skin of a user via a photo detector when measuring a PPG signal, according to an embodiment.

When measuring a PPG signal of a user via an optical sensor biosignal measurement apparatus according to the present embodiment, the change in the DC level of the quantity of light over time, detected by the photo detector, may be shown as the graph of FIG. 5.

In FIG. 5, each of a first threshold value and a second threshold value indicates the DC level of the quantity of light that the PPG signal may measure. Specifically, it may be set so that a normal PPG signal may be measured when the DC level of the quantity of light is between the first threshold value and the second threshold value.

In this case, the user's normal PPG signals may be measured for sections A and C, respectively. However, for other sections B and D, the strength of the quantity of light transmitted to the photo detector 130 drastically increases due to disturbance light and the like. Accordingly, when the DC level of the quantity of light is greater than the first threshold value, it is difficult to measure a normal PPG signal.

Accordingly, the light quantity controller 140 determines whether the DC level of the quantity of light detected by the photo detector 130 is greater than the first threshold value for a predetermined period of time. In this instance, the predetermined period of time, the first threshold value, and the second threshold value may be appropriately set depending on judgments of those of skilled in the art.

As shown in the section D, when the DC level of the quantity of light detected by the photo detector 130 is greater than the first threshold value for at least as long as the predetermined period of time, the light quantity controller 140 determines that the effect of disturbance light continuously occurs and thereby may control the light quantity adjustment member 120 to reduce the optical transmission area of the photo detector 130.

Also, as shown in the section B, when the DC level of the quantity of light detected by the photo detector 130 is in excess of the first threshold value for less than the predetermined period of time, the quantity light controller 140 may determine the effect of disturbance light occurred momentarily. Accordingly, the light quantity controller 140 may control the biosignal information generator 150 to eliminate a peak value of the DC level of the quantity of light momentarily in excess of the first threshold value and thereby generate biosignal information.

Also, when the detected DC level of the quantity of light is less than the second threshold value, the light quantity controller 140 may determine that an insufficient amount of light is emitted towards the skin of the user 101, and control the luminous element 110 to increase the strength of light emitted towards the skin of the user 101 via the luminescence controller 160.

As described above with reference to FIG. 5, the light quantity controller 140 may detect the DC level of the quantity of light detected from the skin of the user 101 via the photo detector 130 in real time, and thereby determine whether the appropriate quantity of light is detected. Also, based on the result of the determination, the light quantity controller 140 may control the light quantity adjustment member 120 to adjust the optical transmission area or the optical transmittance of the photo detector 130. Also, when it is determined that the effect of disturbance light is momentary, the light quantity controller 140 may exclude the instant effect of momentary disturbance light and thereby control the biosignal information generator 150 to generate the user's biosignal information.

Figure 6:
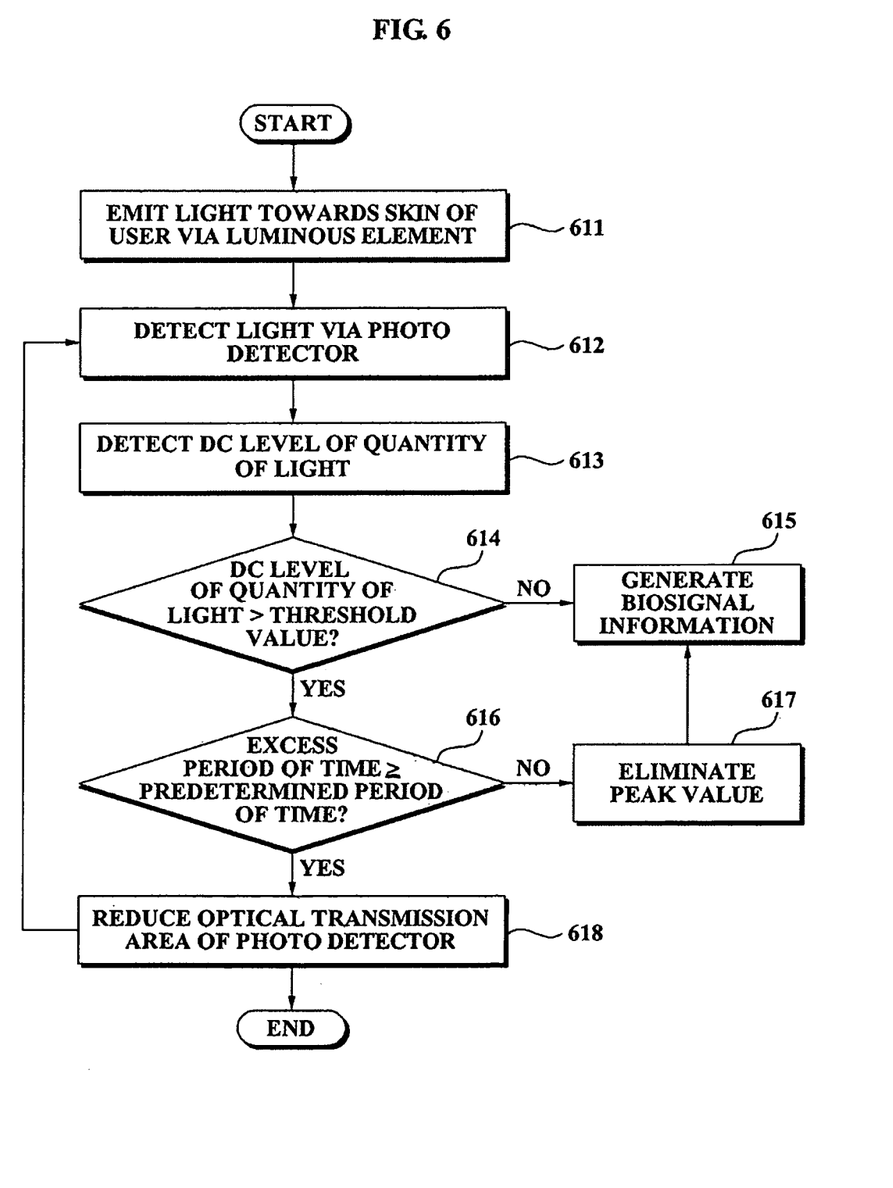
FIG. 6 is a flowchart illustrating a method of controlling an optical sensor of an optical sensor biosignal measurement apparatus according to an embodiment.

FIG. 6 is a flowchart illustrating a method of controlling an optical sensor of an optical sensor biosignal measurement apparatus according to an embodiment.

In operation 611, the optical sensor biosignal measurement apparatus emits light towards the skin of a user via a luminous element of the optical sensor. In operation 612, the optical sensor biosignal measurement apparatus detects the light from the skin of the user via a photo detector of the optical sensor. In operation 613, the optical sensor biosignal measurement apparatus detects a DC level of the quantity of light.

In operation 614, the optical sensor biosignal measurement apparatus compares the detected DC level of the quantity of light with a predetermined threshold value. When the DC level of the quantity of light is less than or equal to the threshold value in operation 614, the optical sensor biosignal measurement apparatus generates the user's biosignal information by using the light detected via the photo detector in operation 615.

Conversely, when the DC level of the quantity of light is greater than the threshold value in operation 614, the optical sensor biosignal measurement apparatus determines whether the DC level of the quantity of light is greater than the threshold value for at least as long as a predetermined period of time in operation 616.

When the DC level of the quantity of light is in excess of the threshold value for less than the predetermined period of time in operation 616, the optical sensor biosignal measurement apparatus determines that the effect of disturbance light is momentary and thereby eliminates the DC level of the quantity of light in excess of the threshold value in operation 617, and generates the user's biosignal information in operation 615.

Conversely, when the DC level of the quantity of light is greater than the threshold value for at least as long as the predetermined period of time in operation 616, the optical sensor biosignal measurement apparatus determines that the effect of disturbance light continuously exists and thereby controls a light quantity adjustment member to reduce an optical transmission area of the photo detector in operation 618, and again performs operation 612.

In operation 618, when the light quantity adjustment member is a diaphragm, the optical sensor biosignal measurement apparatus may reduce an open area and a closed area of a diaphragm and thereby adjust the optical transmission area of the photo detector.

Also, in operation 618, when the light quantity adjustment member is at least one PDLC unit, the optical sensor biosignal measurement apparatus may control a current supply with respect to the at least one PDLC unit and thereby reduce the optical transmission area of the photo detector.

Also, in operation 618, when the light quantity adjustment member is an LCD unit, the optical sensor biosignal measurement apparatus may reduce an optical transmittance of the LCD unit and thereby reduce the optical transmission area of the photo detector.

The method of controlling the optical sensor of the optical sensor biosignal measurement apparatus according to the above-described embodiments may be recorded in computer-readable media including program instructions to implement various operations embodied by a computer. The media may also include, alone or in combination with the program instructions, data files, data structures, and the like. Examples of computer-readable media include magnetic media, such as hard disks, floppy disks, and magnetic tape; optical media, such as CD ROM disks and DVD; magneto-optical media such as optical disks; and hardware devices that are specially configured to store and perform program instructions, such as read-only memory (ROM), random access memory (RAM), flash memory, etc. The media may also be a transmission medium, such as optical or metallic lines, wave guides, etc. including a transmitting signals specifying the program instructions, data structures, etc. Examples of program instructions include both machine code, such as produced by a compiler, and files containing higher level code that may be executed by the computer using an interpreter. The described hardware devices may be configured to act as one or more software modules in order to perform the operations of the above-described embodiments.

According to the above-described embodiments, there is provided an optical sensor biosignal measurement apparatus which can install a diaphragm in a photo detector of an optical sensor, appropriately adjust an optical transmission area of the photo detector via the diaphragm, and reduce effects of disturbance light, and thereby can more accurately measure a biosignal without restriction on time and occasion, and a method of controlling an optical sensor of the apparatus.

Also, according to the above-described embodiments, there is provided an optical sensor biosignal measurement apparatus which can install at least one PDLC unit in a photo detector of an optical sensor, appropriately adjust an optical transmission area of the photo detector via the at least one PDLC unit, and reduce effects of disturbance light, and thereby can more accurately measure a biosignal without restriction on time and occasion, and a method of controlling an optical sensor of the apparatus.

Also, according to the above-described embodiments, there is provided an optical sensor biosignal measurement apparatus which can install an LCD unit in a photo detector of an optical sensor, appropriately adjust an optical transmission area of the photo detector via the LCD unit, and reduce effects of disturbance light, and thereby can more accurately measure a biosignal without restriction on time and occasion, and a method of controlling an optical sensor of the apparatus.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. An optical sensor biosignal measurement apparatus comprising:
   an optical sensor having a luminous element emitting light towards skin of a user and a photo detector detecting light from the skin of the user;
   a light quantity adjustment member adjusting an optical transmission area of the photo detector; and
   a light quantity controller detecting a quantity of the light detected by the photo detector, and controlling the light quantity adjustment member to adjust the optical transmission area of the photo detector,
   wherein the quantity of the light detected exceeding a threshold value is excluded when the quantity of the light detected exceeds the threshold value for less than a first predetermined period of time, and the optical transmission area is adjusted when the quantity of the light detected continuously exceeds the threshold value for a second predetermined period of time.

2. The optical sensor biosignal measurement apparatus of claim 1, wherein the first predetermined period of time and the second predetermined period of time are the same.

3. The optical sensor biosignal measurement apparatus of claim 1, wherein the light quantity adjustment member is a diaphragm, and
   the light quantity controller controls an open area and a closed area of the diaphragm to adjust the optical transmission area of the photo detector.

4. The optical sensor biosignal measurement apparatus of claim 1, wherein the light quantity adjustment member is at least one polymer-dispersed liquid crystal (PDLC) unit, and
   the light quantity controller controls a current supply with respect to the at least one PDLC unit to adjust the optical transmission area of the photo detector.

5. The optical sensor biosignal measurement apparatus of claim 4, wherein the at least one PDLC unit includes a plurality of PDLC units, and the current supply is selectively supplied to at least one of the plurality of PDLC units and is not supplied to at least one of the plurality of PDLC units.

6. The optical sensor biosignal measurement apparatus of claim 5, wherein when a first PDLC unit is not supplied current, the optical transmission area is a second area or a third area, excluding a first area.

7. The optical sensor biosignal measurement apparatus of claim 1, wherein the light quantity adjustment member is a liquid crystal display (LCD) unit, and the light quantity control unit controls an optical transmittance of the LCD unit to adjust the optical transmission area of the photo detector.

8. The optical sensor biosignal measurement apparatus of claim 1, wherein the light quantity controller detects a direct current (DC) level of the quantity of light detected by the photo detector, compares the DC level of the quantity of light with the threshold value for the second predetermined period of time, and controls the light quantity adjustment member to reduce the optical transmission area of the photo detector when the DC level of the quantity of light is greater than the threshold value for at least as long as the second predetermined period of time, as a result of the comparison.

9. The optical sensor biosignal measurement apparatus of claim 8, further comprising: a biosignal information generator generating the user's biosignal information by using the light detected by the photo detector,
   wherein the light quantity controller controls the biosignal information generator to eliminate the DC level of the quantity of light in excess of the threshold value and thereby generate the user's biosignal information when the DC level of the quantity of light is in excess of the threshold value for less than the first predetermined period of time, as a result of the comparison, while the optical transmission area maintains its original area.

10. A method of controlling an optical sensor of an optical sensor biosignal measurement apparatus, the method comprising:
    detecting light from skin of a user using a photo detector including a light quantity adjustment member;
    detecting a DC level of the detected quantity of light;
    comparing the DC level of the quantity of light with a threshold value for a first or second predetermined period of time; and
    controlling the light quantity adjustment member to reduce an optical transmission area of the photo detector,
    wherein the detected DC level of the quantity of the light exceeding the threshold value is excluded when the DC level of the quantity of the light detected exceeds the threshold value for less than the first predetermined period of time, and the optical transmission area is reduced when the detected DC level of the quantity of light is continuously greater than the threshold value for at least as long as the second predetermined period of time, as a result of the comparison.

11. The method of claim 10, further comprising:
    eliminating the DC level of the quantity of light in excess of the threshold value and thereby generating the user's biosignal information when the DC level of the quantity of light is in excess of the threshold value for less than the first predetermined period of time, as a result of the comparison, while the optical transmission area maintains its original area.

12. The method of claim 10, wherein the controlling of the light quantity adjustment member reduces an open area and a closed area of a diaphragm and thereby adjusts the optical transmission area of the photo detector when the light quantity adjustment member is the diaphragm.

13. The method of claim 10, wherein the controlling of the light quantity adjustment member controls a current supply with respect to at least one PDLC unit and thereby reduces the optical transmission area of the photo detector when the light quantity adjustment member is the at least one PDLC unit.

14. The method of claim 13, wherein when a first PDLC unit is not supplied current, the optical transmission area is a second area or a third area, excluding a first area.

15. The method of claim 10, wherein the controlling of the light quantity adjustment member reduces an optical transmittance of the LCD unit and thereby reduces the optical transmission area of the photo detector.

16. A computer-readable recording medium storing a program executable on a computer to implement a method of controlling an optical sensor of an optical sensor biosignal measurement apparatus, the method comprising:
    detecting light from skin of a user using a photo detector including a light quantity adjustment member;
    detecting a DC level of the detected quantity of light;
    comparing the DC level of the quantity of light with a threshold value for a first or second predetermined period of time; and
    controlling the light quantity adjustment member to reduce an optical transmission area of the photo detector,
    wherein the detected DC level of the quantity of the light exceeding the threshold value is excluded when the DC level of the quantity of the light detected exceeds the threshold value for less than the first predetermined period of time, and the optical transmission area is reduced when the detected DC level of the quantity of light is continuously greater than the threshold value for at least as long as the second predetermined period of time, as a result of the comparison.

17. A method of controlling an optical sensor of an optical sensor biosignal measurement apparatus, the method comprising:
    detecting a quantity of light from skin of a user with a photo detector; and excluding a DC level of the detected quantity of light exceeding a first threshold value when the DC level of the quantity of the light detected exceeds the threshold value for less than a first predetermined period of time, and reducing the optical transmission area when the DC level of the detected quantity of light continuously exceeds the first threshold value for a second predetermined period of time.

18. The method according to claim 17, further comprising eliminating a peak value of the DC level of the quantity of light when the DC level of the detected quantity of light exceeds the first threshold value for less than the predetermined period of and generating biosignal information based on the DC level of the quantity of light, excluding the eliminated peak value of the DC level of the quantity of light, while the optical transmission area maintains its original area.

19. The method according to claim 17, further comprising increasing a strength of the light emitted toward the skin of the user to detect the quantity of light form the skin of the user when the detected quantity of light is less than a second threshold value.

20. An optical sensor biosignal measurement apparatus, comprising:
    a light quantity controller adjusting an optical transmission area of a photo detector detecting a quantity of light from skin of a user,
    wherein the detected quantity of the light exceeding the threshold value is excluded when the quantity of the light detected exceeds the threshold value for less than a first predetermined period of time, and the optical transmission area is adjusted when the detected quantity of light from the skin of the user continuously exceeds the threshold value for a second predetermined period of time.

21. An optical sensor biosignal measurement apparatus comprising:
    an optical sensor having a luminous element emitting light towards skin of a user and a photo detector detecting light from the skin of the user;
    a light quantity adjustment member adjusting an optical transmission area of the photo detector;
    a light quantity controller detecting a quantity of the light detected by the photo detector and controlling the light quantity adjustment member to adjust the optical transmission area of the photo detector, the adjusting being based on a determination of whether the quantity of the light detected exceeds a threshold value for a predetermined period of time;
    wherein the light quantity controller detects a direct current (DC) level of the quantity of light detected by the photo detector, compares the DC level of the quantity of light with the threshold value for the predetermined period of time, and controls the light quantity adjustment member to reduce the optical transmission area of the photo detector when the DC level of the quantity of light is greater than the threshold value for at least as long as the predetermined period of time, as a result of the comparison, and
    a biosignal information generator generating the user's biosignal information by using the light detected by the photo detector,
    wherein the light quantity controller controls the biosignal information generator to eliminate the DC level of the quantity of light in excess of the threshold value and thereby generate the user's biosignal information when the DC level of the quantity of light is in excess of the threshold value for less than the predetermined period of time, as a result of the comparison, while the optical transmission area maintains its original area.

* * * * *

UNITED STATES PATENT AND TRADEMARK OFFICE
CERTIFICATE OF CORRECTION

PATENT NO. : 8,655,425 B2
APPLICATION NO. : 12/010560
DATED : February 18, 2014
INVENTOR(S) : Kim et al.

Page 1 of 1

It is certified that error appears in the above-identified patent and that said Letters Patent is hereby corrected as shown below:

In the Claims

Column 11, Line 52, In Claim 18, after "period of" insert -- time --.
Column 12, Line 3, In Claim 19, delete "form" and insert -- from --, therefor.
Column 12, Line 27, In Claim 21, delete "detector" and insert -- detector, --, therefor.

Signed and Sealed this
First Day of July, 2014

Michelle K. Lee
*Deputy Director of the United States Patent and Trademark Office*